United States Patent [19]

Gailly et al.

[11] Patent Number: 4,867,977

[45] Date of Patent: Sep. 19, 1989

[54] CALCIUM SALTS

[75] Inventors: Jean-Marc Gailly; Daniel Gomez; Burguiéne Martine, all of Orléans; André Gens, Olivet; Jean Remy, St. Cyr en Val, all of France

[73] Assignee: Sandoz, Ltd., Basel, Switzerland

[21] Appl. No.: 67,311

[22] Filed: Jun. 26, 1987

[30] Foreign Application Priority Data

Jul. 1, 1986 [FR] France ............................ 8609515

[51] Int. Cl.$^4$ ............... A61K 33/06; A61K 33/10; A61K 9/46
[52] U.S. Cl. ............................ 424/687; 424/44; 424/466; 426/590; 426/591
[58] Field of Search ................ 424/44, 156, 466; 426/590, 591

[56] References Cited

U.S. PATENT DOCUMENTS

| | | | |
|---|---|---|---|
| 1,526,981 | 2/1925 | Heyl | 424/44 |
| 1,616,587 | 2/1927 | Little | 424/44 |
| 1,765,867 | 6/1930 | Granger | 424/156 |
| 2,603,569 | 7/1952 | Alther et al. | 426/591 |
| 2,639,238 | 5/1953 | Alther et al. | 426/591 |
| 3,061,445 | 10/1962 | Stanish | 426/591 |
| 3,082,091 | 3/1963 | Smith | 426/591 |
| 3,105,792 | 10/1963 | White | 424/44 |
| 3,241,977 | 3/1966 | Mitchell et al. | 424/44 |
| 3,328,304 | 6/1967 | Globus | 424/156 |
| 3,489,572 | 1/1970 | Kracauer | 426/591 |
| 3,939,289 | 2/1976 | Hornyak et al. | 426/591 |
| 3,949,098 | 4/1976 | Bangert | 426/590 |
| 3,965,273 | 6/1976 | Stahl | 426/591 |
| 4,009,292 | 2/1977 | Finucane | 426/591 |
| 4,206,244 | 6/1980 | Schenk | 426/588 |
| 4,237,147 | 12/1980 | Merten et al. | 426/591 |
| 4,551,342 | 11/1985 | Nakel et al. | 426/591 |
| 4,650,669 | 3/1987 | Alexander et al. | 424/466 |
| 4,678,661 | 7/1987 | Gergely et al. | 424/156 |
| 4,725,427 | 2/1988 | Ashmead et al. | 424/44 |
| 4,760,138 | 7/1988 | So et al. | 424/44 |

*Primary Examiner*—Shep K. Rose
*Attorney, Agent, or Firm*—Richard T. Laughlin

[57] ABSTRACT

A solid stable sugar free and sodium free calcium pharmaceutical composition is disclosed comprising a calcium organic salt, calcium carbonate and an organic polycarboxylic acid.

12 Claims, No Drawings

CALCIUM SALTS

The present invention relates to pharmaceutical compositions containing calcium salts, especially for oral administration.

Calcium salts are well known for the treatment of calcium deficiencies and their symptoms. For an acceptable and effective therapy, calcium pharmaceutical compositions based on such salts must have a high content of calcium ions in order to facilitate the assimilation into the body of a sufficient amount of calcium. Moreover, for permanent calcium therapy in practice only oral administration comes into question. One wellestablished oral calcium pharmaceutical composition comprises an effervescent tablet containing calcium gluconolactate (also known as calcium lactogluconate and calcium lactategluconate), calcium carbonate, sodium bicarbonate, citric acid and sucrose. Before administration, the tablet is dissolved in a glass of water to give a sparkling (effervescent) drink. For permanent therapy, such a composition with its sodium and sucrose content may be unsatisfactory for subjects only allowed to take foods and medicines having a low content of sodium ions or for diabetic subjects. Moreover, the sparkling drink may lead to digestive and gastric disorders.

After extensive testing we have now found an advantageous stable, sugar-free and sodium-free or substantially sodium-free calcium composition which not only provides a high dose of calcium ions per unit dosage but is easily and quickly dissolved in water. It also may be formulated to contain as few excipients as possible which could induce side effects.

In one aspect, the present invention provides a stable, sugar-free and sodium-free or substantially sugar and sodium-free calcium pharmaceutical composition, comprising a calcium organic salt, calcium carbonate and a non-aromatic organic polycarboxylic acid.

In another aspect the present invention provides a process comprising mixing the above constituents.

Appropriate calcium organic salts used in the compositions of the invention, preferably have calcium ion contents of above 5 or even 10 percent. They include for example calcium glucoheptonate, calcium ascorbate, calcium gluconate, calcium lactate, calcium gluconolactate, calcium citrate, calcium fumarate and calcium levulinate. Preferably, the calcium organic salt is the calcium salt of gluconic acid and/or lactic acid, particularly calcium gluconate, calcium lactate and calcium gluconolactate, more preferably calcium gluconolactate. These calcium organic salts are known; calcium gluconolactate may be prepared for example as described in the US Pat. No. 1 267 760. Calcium gluconolactate has a calcium content of about 12-13%, e.g. 12,92% by weight.

The organic polycarboxylic acid used in the compositions of the invention is preferably a low molecular weight acid, e.g. of up to 6 carbon atoms, and conveniently fumaric acid or an organic hydroxy polycarboxylic acid such as tartaric acid, malic acid or citric acid. The organic polycarboxylic acid is preferably citric acid. Preferably the acids are used in anhydrous form.

The compositions of the invention provide high amounts of calcium ions. Per dosage, the total amount of calcium organic salt and calcium carbonate is chosen to provide conveniently from about 200 mg to about 1000 mg of calcium ions, preferably about 500 mg. The weight ratio of calcium organic salt to calcium carbonate is conveniently from 35:1 to 5:1, preferably between 25:1 and 8:1, and may be for example ca. 23:1 or 10:1.

The weight ratio of calcium carbonate to the organic polycarboxylic acid is conveniently from 1:3 to 1:6, for example from 1:3.5 to 1:4.5, and is preferably of about 1:4.

The pH of the aqueous solution produced on dissolving the compositions of the invention is conveniently between 3.6 and 4, for example from 3.75 to 3.92, in e.g. 100 ml water.

Preferably the compositions of the invention contain a non-carbohydrate sweetener agent. Appropriate non-carbohydrate sweetener agents include L-aspartyl-L-phenylalanine methylester (known as Aspartam ®), cyclamic acid or its calcium salt or preferably a saccharinate, e.g. ammonium or especially calcium saccharinate. When the compositions of the invention contain a noncarbohydrate sweetener agent, the weight ratio of the non-carbohydrate sweetener agent to calcium carbonate is preferably from about 1:5 to 1:20, particularly from 1:7.5 to 1:15.

The compositions of the invention preferably may contain flavouring agents such as lemon, orange, grapefruit, raspberry, strawberry, black currant or apricot flavours, preferably lemon.

If desired, the compositions of the invention may contain up to 0.2% by weight of a flowing agent, preferably colloidal silica (known for example under the name Aerosil).

The compositions of the invention may be completely sodium and sugar-free or may contain, in the light of additional excipients present, only insignificant amounts of sodium. Preferably, such compositions are free of excipients containing sodium and are entirely sodium free.

The compositions of the invention are preferably in the form of a powder. The compositions in the powder form may e.g. have a particle size diameter of from 20 to 1000 microns, preferably from 50 to 750 microns; more especially, at least 80% of the powder has a particle size diameter of from 60 to 500 microns. Such powders may be prepared according known methods, e.g. by dry mixing of the different constituents, for example in a tumbler mixer/blender. In order to obtain a good distribution of the mixture, each constituent may be processed e.g. sieved, before the mixing operation to obtain a similar average particle size for each constituent. Conveniently, the constituents which are present in a low amount in the final composition, such as the non-carbohydrate sweetener agent and the flavouring agent, are diluted in part of the organic polycarboxylic acid or in the calcium salts before mixing with the other constituents.

A particularly preferred composition according to the invention, is a sugar-free and sodium-free composition comprising calcium gluconolactate, calcium carbonate, citric acid, a non-carbohydrate sweetener agent, preferably calcium saccharinate or aspartam, and optionally a flavouring agent, preferably in the weight ratio indicated above for the different constituents. Preferably such a composition is in a powder form.

The resulting powders possess good flowing properties. Surprisingly, the compositions of the invention dissolve well in water in a beaker and in a very short time, for example under 1 minute or even 30 seconds, compared to 3 minutes for the prior art effervescent tablet mentioned above. The compositions of the invention dissolve with only a slight effervescence and give a non-sparkling solution without deposit on the sides of the beaker. They have a good gastric and digestive tolerance. They may be dissolved as indicated in the examples hereinafter.

Clinical tests have shown that the compositions of the invention are well tolerated and have a very acceptable taste. The calcium ions are absorbed well. The compositions of the invention avoid the unfavourable effects on hormones, e.g. PTH, somatotropin C, CRGHP (calcitonin precursor).

The compositions of the invention may be used in therapy for hypocalcaemia to provide high dosages of calcium ions, for example to satisfy the increased demand for calcium in pregnant and lactating women and in growing children, the treatment of osteoporosis, in the treatment of osteopathies, the treatment of rickets and osteomalacia as an adjuvant to specific therapy, in the treatment of tetany and latent tetany, and as a supportive treatment in the treatment of allergic conditions. Due to the absence of sodium and sucrose, the compositions of the invention are particularly appropriate for subjects taking a food regime having a low sodium content or for diabetics. As the resulting solutions are not significantly effervescent, the compositions of the invention are very well accepted for permanent treatments, for example, of osteoporosis.

The compositions of the invention are conveniently in unit dosage forms. The calcium content in the unit dosage may vary depending on e.g. the therapeutic need and may contain the equivalent of e.g. from 200 to 1000 mg calcium, for example 500 mg calcium ions. Preferably, the compositions of the invention in powder form are packed in a sachet for the delivery of a unit dosage, for example 500 mg of calcium. Preferably, the packing comprises paper, aluminium and/or polyethylene or another thermosetting agent. The paper is preferably a paper of 30 to 60 g/m$^2$, e.g. 40 g/m$^2$. Aluminium is preferably an aluminium sheet of 9 to 25 microns in thickness, e.g. 9 microns. Polyethylene is preferably of 20 to 50, e.g. 25 g/m$^2$. The sachet packing comprises preferably 3 layers of paper (outer), aluminium and polyethylene sheets.

Preferably, the weight of the composition in unit dosage form is about 4 to 5 g. Per unit dosage form, the amount of acid is about 0.6 to 0.7 g, e.g. 0.62 to 0.65 g, unless no flavouring agent is present. When a flavouring agent is present, it is preferably about 0.85 to 1.5, e.g. 1.2 to 1.3 g.

Ammonium and calcium saccharinate are also known as saccharin ammonium salt and saccharin calcium salt.

The following examples in which the temperatures are in degrees Centigrade, illustrate the present invention.

EXAMPLE 1

A powder having the following composition is prepared:

| Unit dose content in g | |
| --- | --- |
| | Composition A |
| Calcium gluconolactate | 2.940[1] |
| Calcium carbonate | 0.300[2] |
| Citric acid (anhydrous) | 1.220 |
| Ammonium saccharinate | 0.020 |
| Flavour-lemon or orange (powder) | 0.020 |

| -continued | |
| --- | --- |
| Unit dose content in g | |
| | Composition A |
| Total | 4.500 |

[1] corresponds to 379.85 mg calcium ions
[2] corresponds to 120.12 mg calcium ions In a mixer of 140 liters 29.4 kg of calcium gluconolactate, 3 kg of calcium carbonate (sieved through 0.8 mm mesh) and 12.2 kg of granulated anhydrous citric acid are mixed together for 5 minutes (mixture I). To 1.6 kg of this mixture, 0.2 kg of ammonium saccharinate and 0.2 kg of lemon or orange flavour are added and the resulting mixture is mixed for 5 minutes (mixture II). Mixtures I and II are sieved (1 mm mesh) and mixed together for 10 minutes, to give 45 kg of composition A. The mixture suffices for the filing of 10 000 sachets each containing 4.5 g of the composition A indicated above and containing about 500 mg calcium ions.

EXAMPLE 2

The following compositions B to H may be prepared in analogous manner to that described in Example 1.

| | Unit dose content in g. | | |
| --- | --- | --- | --- |
| | B | C | D |
| Calcium gluconolactate | 3.405 | 2.940 | 3.250 |
| Calcium carbonate | 0.150 | 0.300 | 0.200 |
| Citric acid (anhydrous) | 0.625 | 1.215 | 0.880 |
| Aspartam | — | 0.025 | — |
| Ammonium saccharinate | 0.020 | — | 0.020 |
| Flavour-lemon or orange (powder) | — | 0.020 | 0.050 |
| Total | 4.200 | 4.500 | 4.400 |

| | Unit dose content in g. | |
| --- | --- | --- |
| | E | F |
| Calcium gluconolactate | 3.405 | 2.940 |
| Calcium carbonate | 0.150 | 0.300 |
| Citric acid (anhydrous) | 0.625 | 1.220 |
| Calcium saccharinate | 0.020 | 0.020 |
| Flavour-lemon or orange (powder) | — | 0.020 |
| Total | 4.200 | 4.500 |

| | Unit dose content in g. | |
| --- | --- | --- |
| | G | H |
| Calcium gluconolactate | 2.940 | 3.405 |
| Calcium carbonate | 0.300 | 0.150 |
| Citric acid (anhydrous) | 1.220 | 0.625 |
| Aspartam | 0.020 | 0.020 |
| Flavour-lemon or orange (powder) | 0.020 | — |
| Total | 4.500 | 4.200 |

The compositions obtained in examples 1 to 2 are filled into sachets made from multilayer sheets comprising 40 g/m$^2$ paper, 9 microns thick aluminium and 25 g/m$^2$ thick polyethylene in a sachet filling and packaging machine (e.g. type Wolkogon) producing 80 filled sachets (7 cm$^2$) every minute. The sachet edges are sealed by heat.

The sealed sachets are then packed in groups of 6 units in cardboard boxes. They can be stored for a long period of time without significant alteration of the composition.

To use, the opened sachet content is dissolved in water or, for the non-flavoured compositions, in an aqueous beverage, e.g. orangeade or lemon squash, or fruit juice. Advantageously, the sachet content is poured into a vessel, water or the dissolution liquid being then added to give a quick dissolution of the composition. The amount of liquid to be used to dissolve the content of one sachet may vary according to the user's taste; to achieve complete dissolution, the content of these sachets will be advantageously dissolved in an amount of liquid greater than about 30 ml (e.g. 70–80 ml), if necessary with stirring.

The content of these sachets dissolves in 20 to 30 seconds to give a clear sediment-free solution having an aggreeable taste.

Characteristics of compositions A and B prepared according the above Examples are indicated hereinafter.

|  | Composition A | Composition B |
|---|---|---|
| Flowing rate (100 g of powder) | 5 seconds | 7 seconds |
| Compactness volume (100 g of powder) | | |
| $V_o$ (Poured volume) | 144 ml | 150 ml |
| $V_{10}$ (Tapped volume) | 132 ml | 140 ml |
| $V_{500}$ (Tapped volume) | 114 ml | 118 ml |
| Dissolution rate (100 ml) | 1 min. | 1 min. |
| pH of the solution (100 ml) | 3.75 | 3.92 |

| Particle size diameter | A | B |
|---|---|---|
| less than 63 microns | 4.1% | 4.3% |

|  | A | B |
|---|---|---|
| next fraction greater than 63 microns | 15.5% | 19.2% |
| next fraction greater than 100 microns | 17.4% | 22.8% |
| next fraction greater than 160 microns | 17.2% | 19.3% |
| next fraction greater than 250 microns | 31% | 27.6% |
| next fraction greater than 500 microns | 14.65% | 7.8% |

Flowing rate test 100 g of powder are introduced in a standardized funnel and the time measured for the powder to flow through into a graduated cylinder. For powders having good flowing properties, the flowing time is less than 10 seconds.

Tapped volume test

The volume of the powder in the graduated cylinder from the flowing rate test is determined before tapping (Vo) and after 10 ($V_{10}$) and 500 tappings ($V_{500}$). For powders having good flowing properties, the difference $V_{10}-V_{500}$ must be less than 25 ml.

I claim:

1. A stable, sugar free and substantially sodium free calcium pharmaceutical composition in powder form consisting essentially of a calcium organic salt of gluconic or lactic acid, calcium carbonate, the weight ratio of the calcium organic salt to calcium carbonate being from 35:1 to 5:1, and a non-aromatic polycarboxylic organic acid selected from the group consisting of fumaric acid, tartaric acid, malic acid or citric acid, the weight ratio of calcium carbonate to organic polycarboxylic acid being between about 1:3 and about 1:6.

2. The pharmaceutical composition according to claim 1, wherein the calcium organic salt is calcium gluconolactate.

3. The pharmaceutical composition according to claim 1, wherein the weight ratio of the calcium organic salt to calcium carbonate comprised between about 25:1 and about 8:1.

4. The pharmaceutical composition according to claim 1, wherein the total content of calcium ions in the composition is about 500 mg. per dosage.

5. The pharmaceutical composition according to claim 1, wherein the organic polycarboxylic acid is citric acid.

6. The pharmaceutical composition according to claim 1, wherein the weight ratio of calcium carbonate to organic polycarboxylic acid is between about 1:3.5 and about 1:4.5.

7. The pharmaceutical composition according to claim 1, wherein the power is in the form of unit dosage having a calcium content which is the equivalent of between about 200 mg. and about 1000 mg. calcium ions.

8. The pharmaceutical composition according to claim 1, wherein the composition is packed in a sachet.

9. The pharmaceutical composition according to claim 1, wherein the composition contains a flavoring agent.

10. The pharmaceutical composition according to claim 1, wherein the composition contains a non-carbohydrate sweetener agent.

11. The pharmaceutical composition according to claim 9, wherein the non-carbohydrate sweetener agent is L-aspartyl-L-phenylalanine.

12. A sugar-free and sodium free composition in powder form consisting essentially of calcium-gluconolactate, calcium carbonate, citric acid and a non-carbohydrate sweetener agent.

* * * * *